United States Patent
Cocchioni

(10) Patent No.: US 8,944,710 B2
(45) Date of Patent: Feb. 3, 2015

(54) CONTAINER FOR A PLURALITY OF DISPOSABLE APPLICATORS COMPRISING A RESERVOIR FOR A SUBSTANCE TO BE APPLIED

(75) Inventor: Pasquale Cocchioni, Spello (IT)

(73) Assignee: Diva International S.R.L., Spello (PG) (IT)

( * ) Notice: Subject to any disclaimer, the term of this patent is extended or adjusted under 35 U.S.C. 154(b) by 548 days.

(21) Appl. No.: 13/260,903

(22) PCT Filed: Apr. 3, 2009

(86) PCT No.: PCT/IT2009/000142
§ 371 (c)(1),
(2), (4) Date: Dec. 14, 2011

(87) PCT Pub. No.: WO2010/113196
PCT Pub. Date: Oct. 7, 2010

(65) Prior Publication Data
US 2012/0076565 A1    Mar. 29, 2012

(51) Int. Cl.
*A46B 11/00*    (2006.01)
*A61F 15/00*    (2006.01)
(Continued)

(52) U.S. Cl.
CPC ............ *A61F 15/001* (2013.01); *A45D 29/007* (2013.01); *A45D 34/04* (2013.01); *A45D 34/06* (2013.01); *A45D 40/18* (2013.01); *A45D 40/26* (2013.01); *B65D 1/24* (2013.01); *B65D 43/16* (2013.01); *B65D 43/161* (2013.01); *B65D 77/0453* (2013.01); *A45D 2200/1009* (2013.01);
(Continued)

(58) Field of Classification Search
CPC ..... A45D 29/007; A45D 34/04; A45D 34/06; A45D 40/18; A45D 40/26; A45D 2200/1009; A45D 2200/1063; A45D 2200/25; A45D 2200/1018; B65D 1/24; B65D 43/16; B65D 43/161; B65D 77/0453; A61F 15/001
USPC .......... 401/118, 125, 128; 206/361, 362, 207, 206/514, 515, 518, 519; 222/23.83, 23.86, 222/23.87, 507, 523, 553, 555, 527; 220/23.83, 23.86, 23.87, 507, 523, 220/553, 555, 527
See application file for complete search history.

(56) References Cited

U.S. PATENT DOCUMENTS

D210,057 S    1/1968    Pfrommer et al.
3,589,544 A *    6/1971    Hannon ........................ 215/252
(Continued)

FOREIGN PATENT DOCUMENTS

EM    001107783-0001    3/2009
EM    001107783-0002    3/2009
(Continued)

OTHER PUBLICATIONS

PCT International Search Report issued for PCT/IT2009/000142 filed Apr. 3, 2009 in the name of Diva International S.R.L.
(Continued)

*Primary Examiner* — David Walczak
*Assistant Examiner* — Jennifer C Chiang
(74) *Attorney, Agent, or Firm* — Steinfl & Bruno LLP

(57) ABSTRACT

A container for disposable applicators is described. The container has a main body section and a coupling portion for coupling a reservoir with the container. The reservoir can contain a substance suitable for the disposable applicators.

13 Claims, 6 Drawing Sheets

(51) Int. Cl.
*A45D 29/00* (2006.01)
*A45D 34/04* (2006.01)
*A45D 34/06* (2006.01)
*A45D 40/18* (2006.01)
*A45D 40/26* (2006.01)
*B65D 1/24* (2006.01)
*B65D 43/16* (2006.01)
*B65D 77/04* (2006.01)

(52) U.S. Cl.
CPC . *A45D 2200/1018* (2013.01); *A45D 2200/1063* (2013.01); *A45D 2200/25* (2013.01)
USPC .................. 401/125; 206/362; 220/23.86

(56) References Cited

U.S. PATENT DOCUMENTS

| | | | |
|---|---|---|---|
| 4,428,493 A * | 1/1984 | McDonough | 220/555 |
| D297,118 S | 8/1988 | Fontana et al. | |
| D297,119 S | 8/1988 | Fontana et al. | |
| D297,775 S | 9/1988 | Sussman | |
| D343,058 S | 1/1994 | Allegre | |
| D351,997 S | 11/1994 | Finnah | |
| D393,798 S | 4/1998 | Joswick | |
| D431,322 S | 9/2000 | Lemoine | |
| 6,138,963 A * | 10/2000 | Malvasio | 248/111 |
| 6,387,068 B1 | 5/2002 | Naughton | |
| D463,658 S | 10/2002 | Lemoine | |
| D463,907 S | 10/2002 | Lemoine | |
| D464,791 S | 10/2002 | Lemoine | |
| D467,808 S | 12/2002 | Hagemann et al. | |
| D474,402 S | 5/2003 | Baerenwald | |
| D492,196 S | 6/2004 | Hyhlik et al. | |
| D503,829 S | 4/2005 | Tanii et al. | |
| D503,830 S | 4/2005 | Tanii et al. | |
| D529,820 S | 10/2006 | Kissner et al. | |
| D530,617 S | 10/2006 | Little et al. | |
| D539,135 S | 3/2007 | Blasko et al. | |
| D540,169 S | 4/2007 | Tanner | |
| D540,189 S | 4/2007 | Larocca | |
| D540,190 S | 4/2007 | Larocca | |
| D543,862 S | 6/2007 | Miller et al. | |
| D545,186 S | 6/2007 | Liebe et al. | |
| D548,589 S | 8/2007 | Blasko et al. | |
| D551,072 S | 9/2007 | Blasko et al. | |
| D551,963 S | 10/2007 | Blasko et al. | |
| D551,964 S | 10/2007 | Blasko et al. | |
| D551,965 S | 10/2007 | Blasko et al. | |
| D551,966 S | 10/2007 | Blasko et al. | |
| D553,491 S | 10/2007 | Blasko et al. | |
| D585,735 S | 2/2009 | Vovan et al. | |
| D588,915 S | 3/2009 | Lohrman et al. | |
| D601,416 S | 10/2009 | Fosse et al. | |
| D613,606 S | 4/2010 | Pavy et al. | |
| D617,043 S | 6/2010 | Patel et al. | |
| D625,597 S | 10/2010 | Wichowski | |
| D644,124 S | 8/2011 | Cocchioni et al. | |
| D644,125 S | 8/2011 | Cocchioni et al. | |

FOREIGN PATENT DOCUMENTS

| | | |
|---|---|---|
| EM | 001107783-0003 | 3/2009 |
| EM | 001107783-0004 | 3/2009 |
| EM | 001107783-0005 | 3/2009 |
| EM | 001107783-0006 | 3/2009 |
| EM | 001107783-0007 | 3/2009 |
| EM | 001107783-0008 | 3/2009 |
| EM | 001107783-0009 | 3/2009 |
| EM | 001107783-0010 | 3/2009 |
| EM | 001107783-0011 | 3/2009 |
| EM | 001107783-0012 | 3/2009 |
| EM | 001107783-0013 | 3/2009 |
| EM | 001107783-0014 | 3/2009 |
| EM | 001107783-0015 | 3/2009 |
| EM | 001107783-0016 | 3/2009 |
| EM | 001107783-0017 | 3/2009 |
| EM | 001107783-0018 | 3/2009 |
| EM | 001107783-0019 | 3/2009 |
| EM | 001107783-0020 | 3/2009 |
| EM | 001107783-0021 | 3/2009 |
| EM | 001107783-0022 | 3/2009 |
| EM | 001107783-0023 | 3/2009 |
| EM | 001107783-0024 | 3/2009 |
| EM | 001107783-0025 | 3/2009 |
| EM | 001107783-0026 | 3/2009 |
| EM | 001107783-0027 | 3/2009 |
| EM | 001107783-0028 | 3/2009 |
| EM | 001107783-0029 | 3/2009 |
| EM | 001107783-0030 | 3/2009 |
| EM | 001107783-0031 | 3/2009 |
| EM | 001107783-0032 | 3/2009 |
| EM | 001107783-0033 | 3/2009 |
| EM | 001107783-0034 | 3/2009 |
| EM | 001107783-0035 | 3/2009 |
| EM | 001107783-0036 | 3/2009 |
| EP | 1288134 A1 * | 3/2003 |
| EP | 1731447 A1 * | 12/2006 |
| WO | 02/17744 | 3/2002 |
| WO | 2009/003890 | 1/2009 |
| WO | 2009/007381 | 1/2009 |

OTHER PUBLICATIONS

PCT Written Opinion issued for PCT/IT2009/000142 filed Apr. 3, 2009 in the name of Diva International S.R.L.

Notice of Allowance mailed by the USPTO on Jun. 23, 2011 for design U.S. Appl. No. 29/343,369.

Notice of Allowance mailed by the USPTO on Jun. 23, 2011 for design U.S. Appl. No. 29/343,372.

* cited by examiner

CONTAINER FOR A PLURALITY OF DISPOSABLE APPLICATORS COMPRISING A RESERVOIR FOR A SUBSTANCE TO BE APPLIED

CROSS REFERENCE TO RELATED APPLICATIONS

The present application is the US national stage of International Application PCT/IT2009/000142 filed on Apr. 3, 2009.

The present invention concerns the technical field of containers for disposable applicators and particularly concerns a container for a plurality of disposable applicators comprising a reservoir for a substance to be applied through such applicators.

In the technical fields of sanitation, cosmetics and health and personal hygiene it is felt that there is the need to make a container suitable for containing a plurality of disposable applicators and also for containing a substance to be applied through said applicators.

A classic example is that of containers for disposable hygiene sticks, also known as cotton swabs, in which in some cases such containers need to be able to contain a plurality of disposable sticks and a substance to be applied, like for example a detergent, disinfectant or sanitizing substance, at the same time. A container for disposable sticks of the aforementioned type is described in the international patent application PCT/EP2008/058076.

There is the need to make a further improved container compared to the container described in the aforementioned application PCT/EP2008/058076, which in particular has low production costs and that is able to be used in a simple and reliable way.

The purpose of the present invention is that of making a container that can satisfy the aforementioned requirement in relation to the prior art.

Such a purpose is achieved with a container as defined in general in the attached claim 1.

Advantageous embodiments of a container according to the present invention are defined in the attached dependent claims.

A further purpose of the present invention is that of providing a group of parts as defined in claim 15.

A process as defined in claim 16 is also object of the present invention.

Further characteristics and advantages of the invention shall become clear from the following detailed description, given purely as an example and not for limiting purposes, with reference to the attached drawings, in which.

In the following description, identical or similar elements in the figures have been indicated with identical reference numbers.

Figure 1:
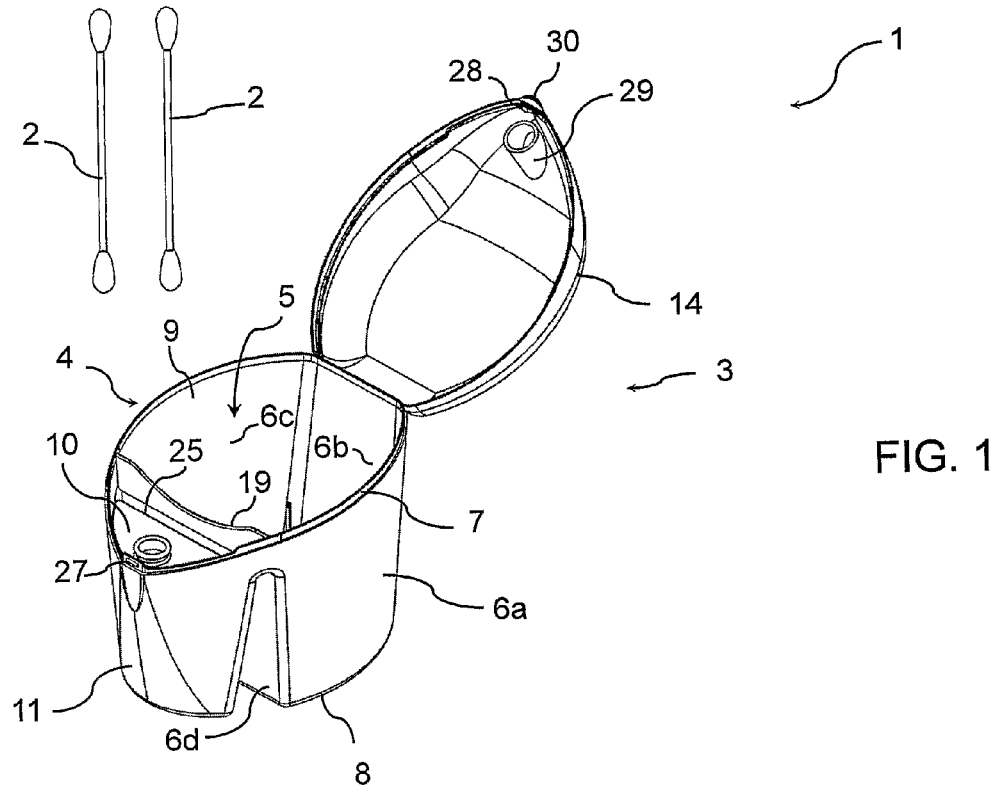
FIG. 1 is an angular perspective view of a group of parts comprising a plurality of disposable applicators, a container for said disposable applicators equipped with a lid and with a reservoir for a substance to be applied.
Figure 2:
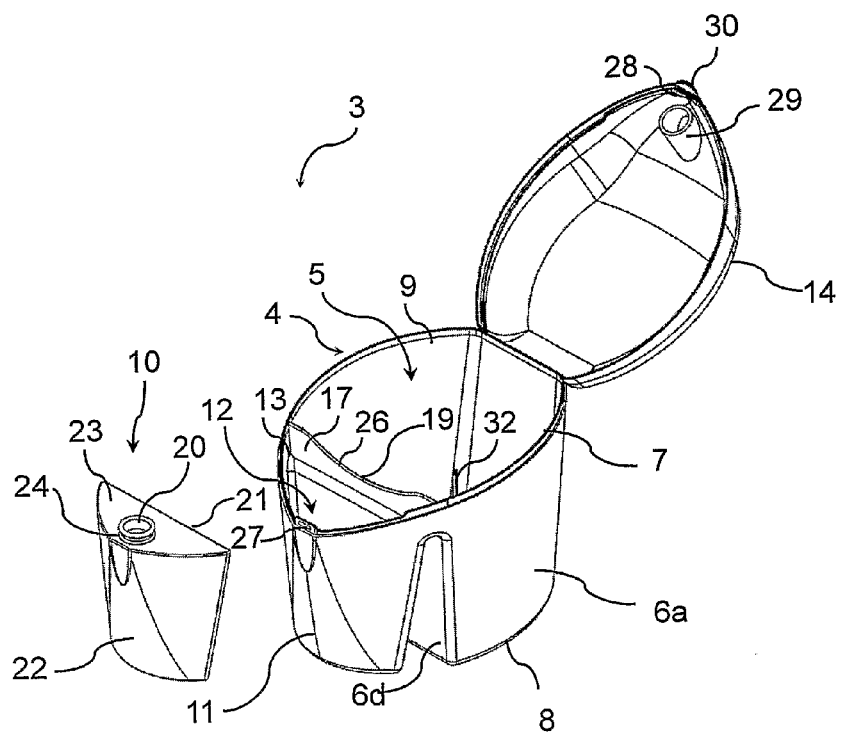
FIG. 2 is an angular perspective view of the container in FIG. 1, in which the reservoir is shown decoupled from the main body of the container.

With reference to the attached figures, reference numeral 1 globally indicates a group of parts, comprising a plurality of disposable applicators 2 (in FIG. 1 only two applicators have been represented as an example, but it is clear that such applicators are generally foreseen in a greater number, for example, not for limiting purposes, equal to 50 or 100) and a container 3 suitable and intended for containing the plurality of disposable applicators 2 and a detergent/sanitizing and/or cosmetic and/or sanitary substance to be applied through the aforementioned applicators 2.

In accordance with a currently preferred embodiment, as represented in the example of FIG. 1, the disposable applicators 2 are cotton swabs, or hygienic sticks, and the substance to be applied is a liquid substance, or a lotion, or a cream, or a gel to be applied for example onto skin or inside the ear. Such a substance is, for example, a disinfectant substance. In another example, such a substance is a solvent, suitable for removing nail polish. As it is known cotton swabs are applicators comprising a stick equipped, at the two opposite end portions, with respective relatively compact cotton padding.

The container 3 comprises a main container body 4 comprising a containment seat 5, defined by at least one side wall 6a-6d and by a bottom wall 8, which in this example is a flat wall. The containment seat 5 is accessible through a first access opening 9 opposite the bottom wall 8. The containment seat 5 is suitable and intended for containing a plurality of disposable applicators 2. In the example of FIG. 1 the disposable applicators 2 are intended for being received inside the containment seat 5, when said seat is full of said applicators 2, parallel to each other and in a vertical position, where by vertical direction we mean, a direction which is perpendicular or substantially perpendicular to the bottom wall 8.

In the example of FIG. 1 the side wall 6a-6d of the main body 4 comprises two opposite curved and rounded walls 6a, 6c and two substantially flat opposite walls 6b, 6d.

The container 3 also comprises a reservoir 10 suitable and intended for containing a detergent/sanitizing and/or cosmetic and/or sanitary substance to be applied through the disposable applicators 2.

The container 3 also comprises a re-closable lid 14 suitable for removably obstructing the containment seat 5 for stopping/giving access to said containment seat. Such a lid 14 is, for example, rotatably hinged to the main body 4 of the container 3. In the example of FIG. 1 the lid 14 is rotatably hinged to the side wall 6b.

The reservoir 10 and the main body 4 form two distinct pieces. In accordance with a currently preferred embodiment, the main body 4 and the reservoir 10 are made out of plastic material, preferably transparent or semitransparent, for example, polythene or polypropylene, the reservoir 10 being made by blowing whereas the main body 4 is made by moulding or injection, preferably integral with the lid 14.

The container 3 comprises a coupling portion 11, integrally made with the main body 4, protruding with respect to the side walls 6a-6d of the main body 4, in the example with respect to the side wall 6d, outwards from the main body 4 and suitable for coupling the reservoir 10 with the main body 4 to fasten the reservoir 10 to the main body 4. In particular, the coupling portion 11 comprises a coupling seat 12 suitable for holding the reservoir 10 in position next to the containment seat 5. In the example represented in FIGS. 1-4, the coupling portion comprises a tray 11, or a pocket 11, suitable for housing the reservoir 10, in position next to the containment seat 5, and more precisely having an access opening 13 in position next to the access opening 9 of the tray 11. With reference to FIG. 4, the tray 11 preferably comprises a flat side wall 15 facing towards the containment seat 5 and an opposite curved and rounded side wall 16. In the example of FIG. 4 the tray 11 also comprises a flat bottom wall 18 preferably parallel to and more preferably on the same plane as the bottom wall 8.

In accordance with an advantageous embodiment, the containment seat 5 and the tray 11 have inclined outer side walls 6a-6d, 15, 16 so as to allow more containers 3 to be stacked interpenetrating each other when the reservoir 10 is not coupled with the container 3 and before filling the container 3 with the disposable applicators 2.

More preferably, as can be observed in FIG. 4, the aforementioned inclined outer side walls 6a-6d, 15, 16 are tapered so as to come together in the direction (indicated with the arrow IV) that leads from the access opening 9 of the containment seat 6 to the bottom wall 8 of the main body 4.

With reference to FIG. 1, the reservoir 10 comprises a top outer wall 23, in which a substance withdrawal opening 20 is defined, and at least one side wall 21, 22. The withdrawal opening 20 allows access inside the reservoir 10, and it is intended for being penetrated by an end portion of a disposable applicator 2 allowing such a portion to be soaked or dipped in the substance contained inside the reservoir 10.

Preferably, the withdrawal opening 20 is surrounded by a raised collar 24, which more preferably has an upper rim laterally protruding with respect to the remaining portion of the raised collar 24 defining an undercut.

In the example represented in FIGS. 1-4, the side wall 21, 22 of the reservoir 10 comprises a bulged side wall 22 and a flat side wall 21 laterally joined together and that close joining at the bottom of the reservoir 10.

In accordance with an embodiment, the reservoir 10, as represented in the attached figures, is configured like a bottle or like a vial. The reservoir 10 is preferably externally shaped so as to make a substantial shape coupling with the inner walls of the tray 11 so it can be received in the tray 11, through an access opening 13, for being removably or irremovably locked inside of it.

In accordance with an advantageous embodiment, as represented in FIG. 1, the access opening 9 of the containment seat 5 and the access opening 13 of the tray 11 are separated from each other by a dividing wall 17 which has an upper rim 19.

Such an upper rim 19 therefore represents a common separation rim between the two openings 9, 13 which in practice represent two partitions of one same single opening 7 of the container 3.

When the reservoir 10 is housed inside the tray 11 the upper rim 19 is advantageously positioned at a greater height than the upper wall 23 of the reservoir 10. This makes it possible to avoid, or at least reduce the probability of, undesired leaks or dripping outside of the reservoir 10, of the substance to be applied, affecting the containment seat 5, since said substance can flow out infiltrating into a gap 25 defined between the reservoir 10 and the inner walls of the tray 11.

Advantageously, means suitable for facilitating the withdrawal of the disposable applicators 2, when the containment seat 5 is substantially full of said applicators 2, can be provided in the container 3. For example, in the embodiment of FIGS. 1-4, in which the disposable applicators 2 are configured as sticks and are intended for being arranged in the containment seat 5 in a vertical position and parallel to each other, such extraction facilitating means comprise a curved profile recess 26 defined in the dividing wall 17.

In accordance with a particularly preferred embodiment, the lid 14 is such that it removably closes the single opening 7 of the container 3, i.e. it simultaneously closes the access opening 9 at the containment seat 5 and the access opening 13 at the tray 11.

Figure 3:
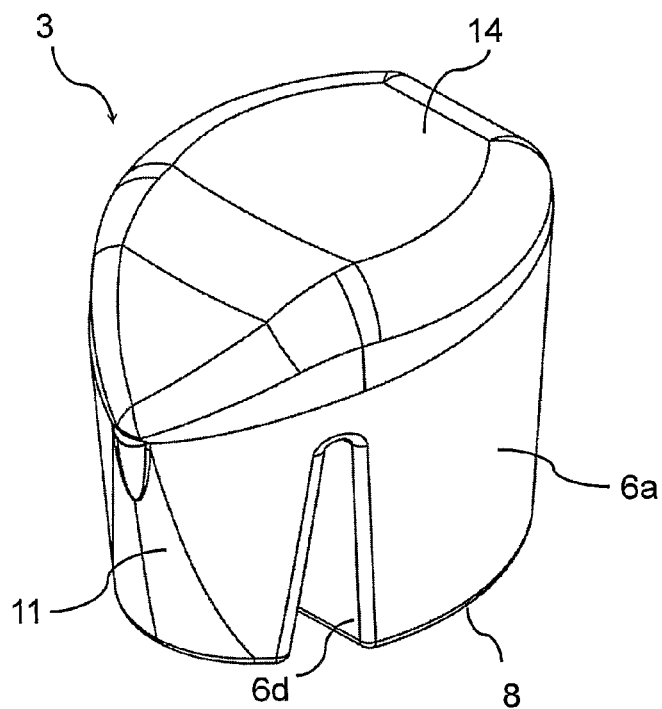
FIG. 3 is an angular perspective view of the container of FIG. 1, in which the container is shown with the lid in the closed position.
Figure 4:
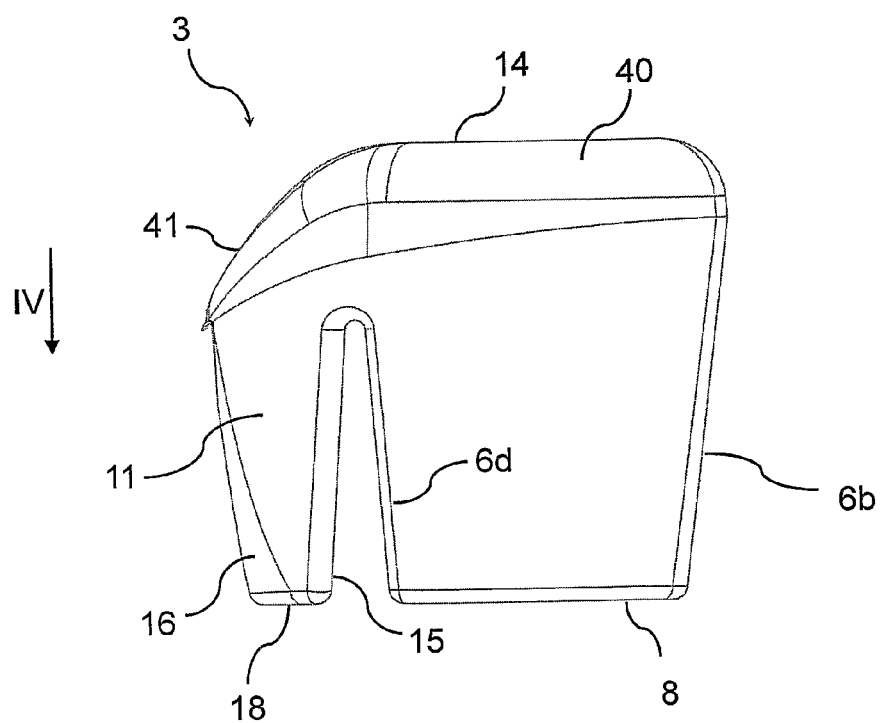
FIG. 4 is a side plane view of the container of FIG. 1, in which the container is shown with the lid in the closed position.

In accordance with an advantageous embodiment, the lid 14 is bulged, having a concavity facing towards the containment seat 5, and comprises a protruding tubular collar 29 opposite the protruding collar 24 of the reservoir 10 and suitable for interfering in abutment with the protruding collar 24 when the lid 14 is in the closed position (FIGS. 3 and 4). Such a protruding collar 29 cooperating with the raised collar 24 makes it possible to avoid or at least reduce the consequences of, undesired leaking from the reservoir 10, of the substance to be applied, when the container 3 is inadvertently tilted.

Advantageously, the container 3 comprises hooking elements 27, 28, for example snap locks, suitable for holding the lid 14 fastened to the remaining part of the container 3 in the closed position. For example, such hooking elements comprise a protruding tooth 28 and a reception recess 27 of such a protruding tooth 28 respectively foreseen in the lid 14 and on one rim of the single opening 7 (or near to such a rim). It is clearly possible to reverse the position of the protruding tooth 28 with that of the reception recess 27.

Preferably, the lid 14 also comprises an ergonomic grip element 30, like for example a gripping tab, suitable for making the opening of the lid 14 easier and more practical for the user.

Inside the containment seat 5, one or more protruding ribs 32 are preferably foreseen, to allow the containers 3 to be separated more easily when two or more containers 3 are stacked into each other.

Finally, it should be observed that in the embodiment represented in FIGS. 1-4, with particular reference to FIGS. 3 and 4, the rounded lid 14 has a first portion 40 facing the containment seat 5 which is centrally flat and laterally rounded and a second portion 41 facing the tray 11 which is rounded but substantially beak shaped and that lowers in height with respect to the first portion 40 to descend towards the tray 11.

As already stated, a container 3 of the aforementioned type can be entirely made by moulding or by injection, with the exception of the reservoir 10 which is advantageously made by blowing. In the process for making said reservoir, the container 3 is therefore provided by moulding or by injection.

It is advantageously possible to stack many containers thus obtained to feed them still stacked into a packaging machine.

Moreover, a reservoir is then made by blowing, and the reservoirs thus obtained are also fed to the packaging machine.

In assembly and in filling, the reservoir 10 is preferably firstly filled with the substance to be applied, possibly subsequently sealing the withdrawal opening 20 with a metallic adhesive tab (not shown in the figures). Thereafter, through the packaging machine, a container 3 is withdrawn from a stack of containers, the reservoir 10 is inserted inside the tray 11, the seat 5 is filled with the disposable applicators 2 and the lid 14 is closed. It should be observed that, if foreseen, the protruding rim of the raised collar 24, forming an undercut, facilitates the automatic gripping of the reservoir 10 through a packaging machine or an industrial robot.

Figure 5:
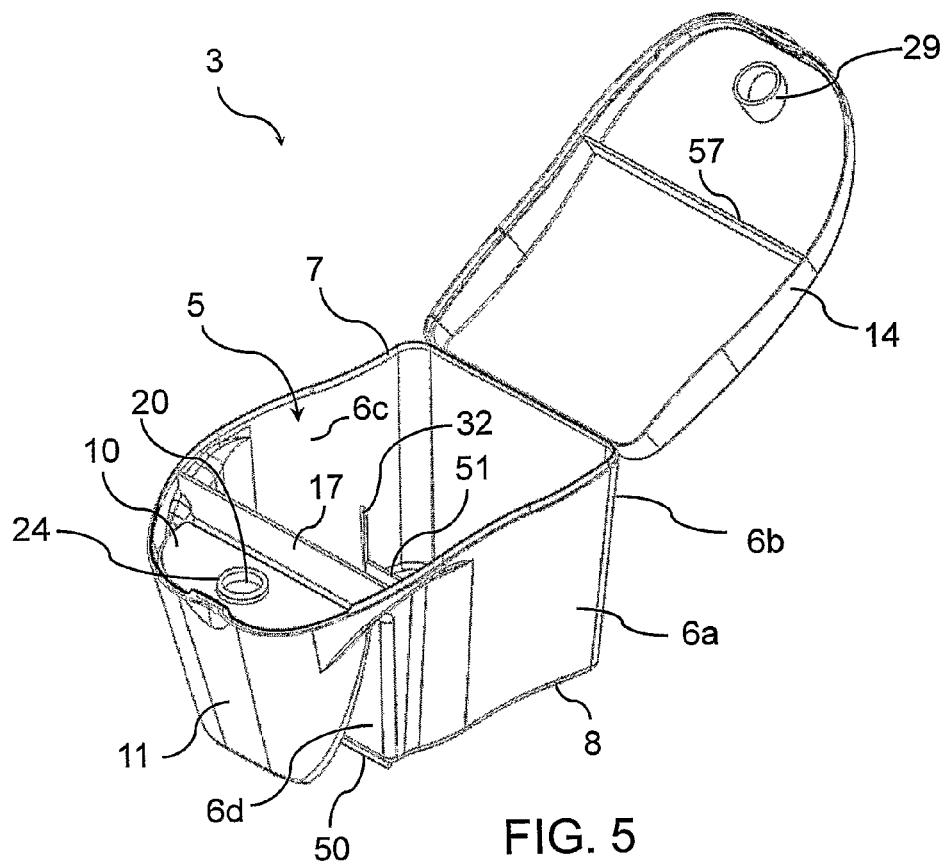
FIG. 5 is an angular perspective view of a first variant embodiment of the container of FIG. 1, in which the container is shown with the lid in the open position.
Figure 6:
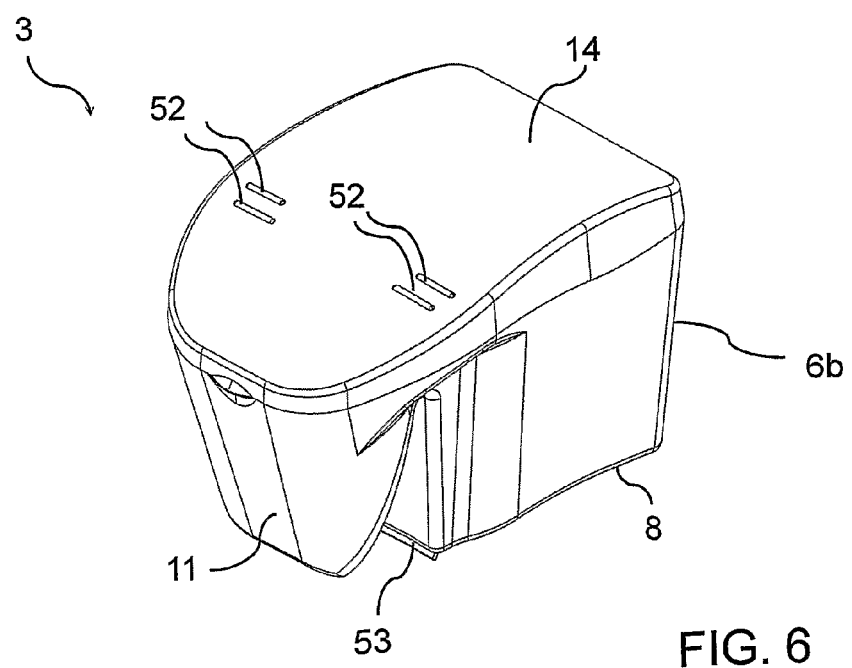
FIG. 6 is an angular perspective view of the container of FIG. 5, in which the container is shown with the lid in the closed position.
Figure 7:
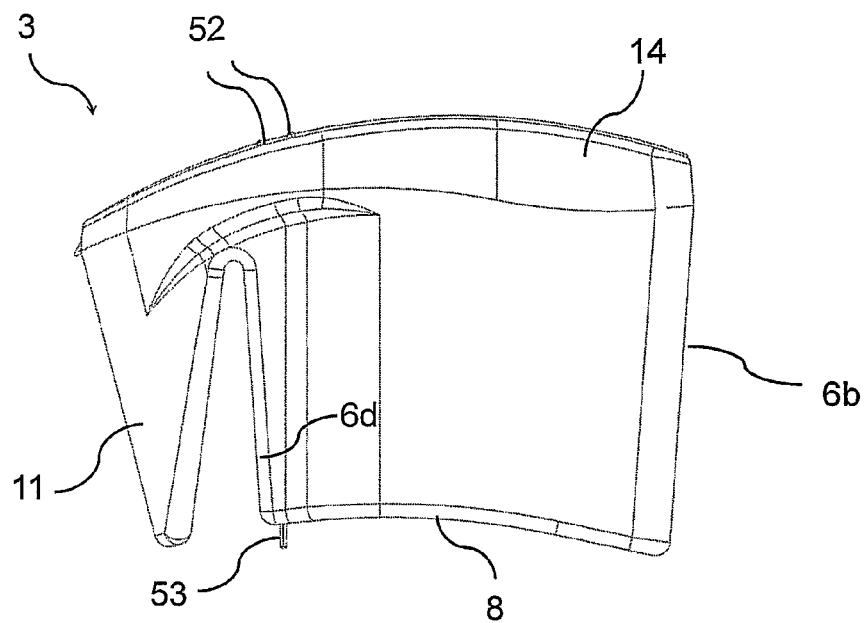
FIG. 7 is a side plane view of the container of FIG. 5 in which the container is shown with the lid in the closed position.

In FIGS. 5 to 7 a variant embodiment of the container 3 is shown, completely similar to the aforementioned embodiment with reference to FIGS. 1-4, with the exception of, as well as the difference in external shape, some differences which shall be illustrated hereafter.

In the container 3 of FIGS. 5-7, the bottom wall 8 of the containment seat 5 is curved instead of being flat. Inside such a container 3 the disposable applicators 2, which are for example cotton swabs 2, are intended to be arranged parallel to each other in a horizontal, or substantially horizontal position. For this reason an alignment wall 51 is foreseen at the bottom of the containment seat 5, which acts as a support for the sticks 2 and allows differences in height of the curved bottom wall 8 to be compensated and therefore keeps the cotton swabs in the horizontal, or substantially horizontal position. Since the sticks 2 are arranged in a horizontal position, the septum 17 does not have the recess 26 (foreseen in the container of FIG. 1 for facilitating the manual withdrawal of the cotton swabs 2 when such a container is full of cotton swabs).

In the container 3 of FIGS. 5-7 a septum 57 is foreseen also on the inner side of the lid 14, which also in this case is bulged, suitable for cooperating with the dividing wall 17 for better insulation of the containment seat 57 when the lid 14 is in the closed position.

On the outer face of the lid 14, one or more non-slip elements 52 are foreseen, which by cooperating with one or more matching non-slip elements 53 foreseen on the outer side of the bottom wall 8, allow many containers 3 to be stacked on top of each other when the lid 14 is in the closed position, for example when stored and when on sale in racks for displaying the containers 3 when they are filled with the disposable applicators 2 and with the substance to be applied. In the particular example described in FIGS. 5-7, the non-slip elements 52, 53 comprise pairs of protruding elements 52, for example in the form of raised notches, at the outer side of the lid 14, and a bar protruding from the bottom wall 8, which acts as a supporting bar, and that is intended to be received between the pairs of protruding elements 52 when two or more containers 3 are stacked one on top of the other with respective lids 14 in the closed position. In a further variant embodiment, it is clearly possible to reverse the position of the pairs of protruding elements 52 with that of the protruding bar 53.

Figure 8:
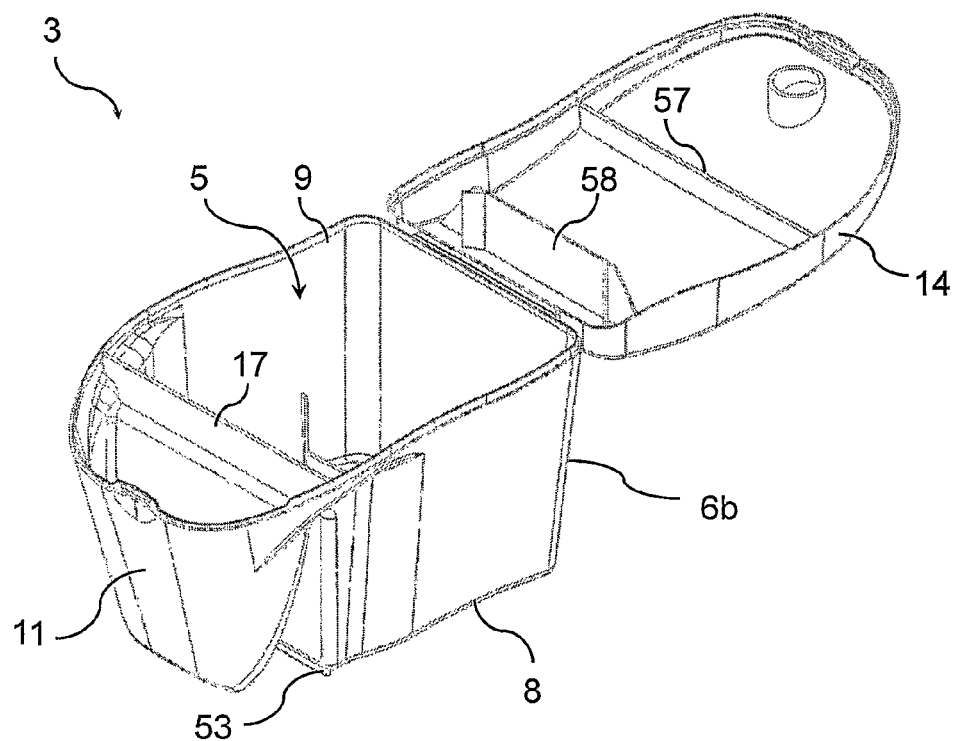
FIG. 8 is an angular perspective view of a second variant embodiment of the container of FIG. 1, similar to the variant embodiment represented in FIGS. 5-7.
Figure 9:
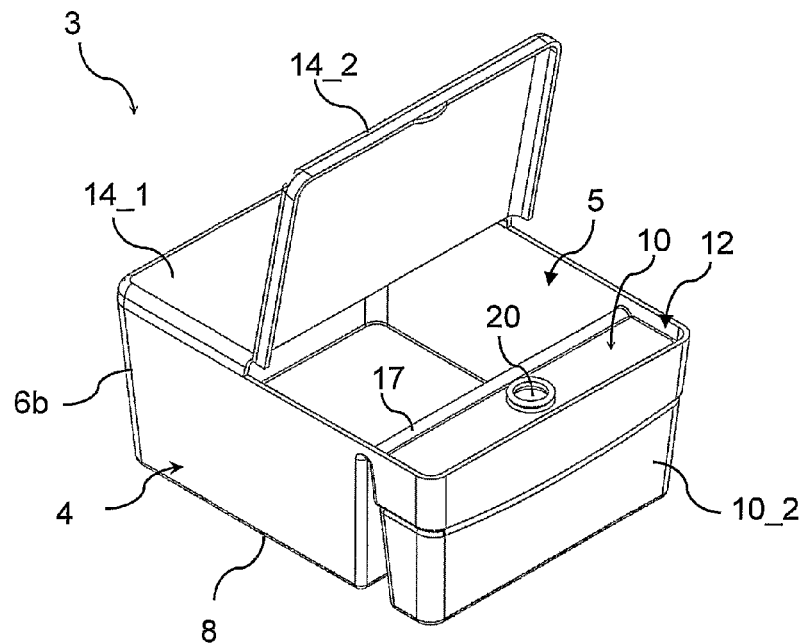
FIG. 9 is an angular perspective view of a third variant embodiment of the container of FIG. 1, in which the container is shown with the lid in the open position.
Figure 10:
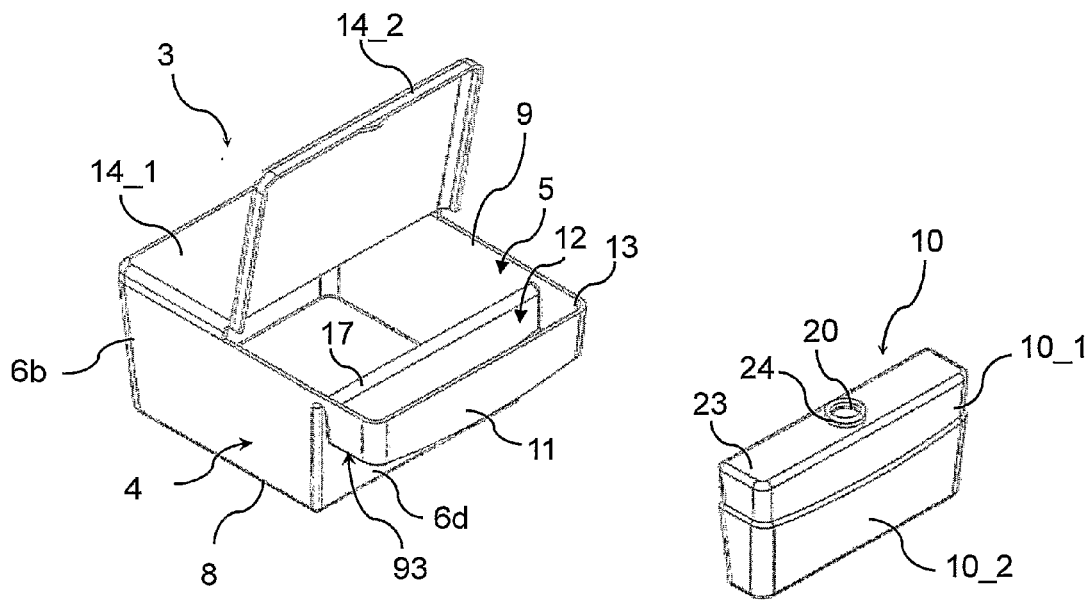
FIG. 10 is an angular perspective view of the container of FIG. 9, in which the reservoir is shown decoupled from the main body of the container.
Figure 11:
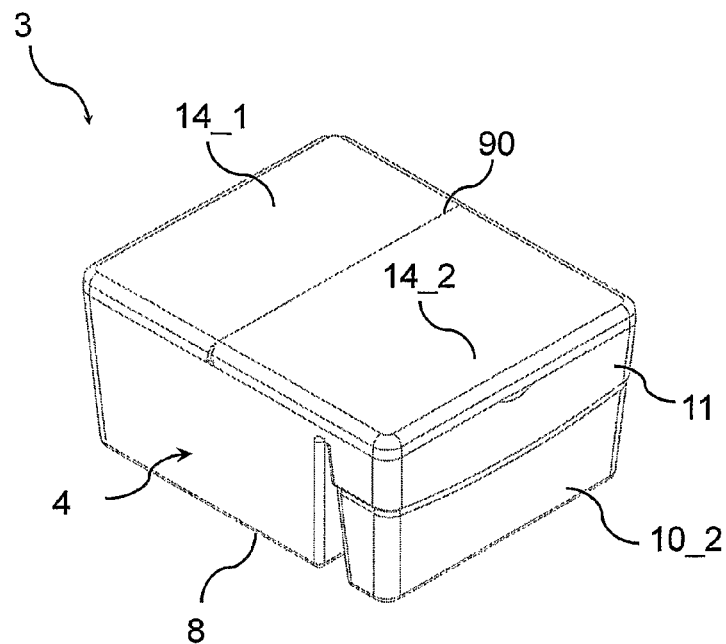
FIG. 11 is an angular perspective view of the container of FIG. 9, in which the container is shown with the lid in the closed position.
Figure 12:
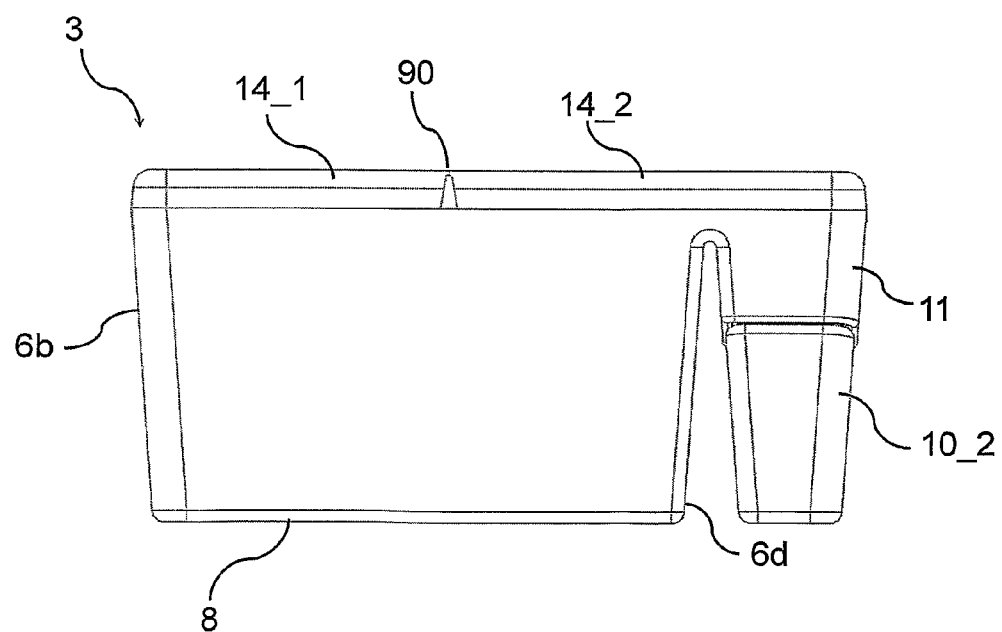
FIG. 12 is a side plane view of the container of FIG. 9 in which the container is shown with the lid in the closed position.

In FIG. 8 a further variant embodiment of the container 3 is shown, which is completely similar to the one just described above with reference to FIGS. 5-7, and that differs from it in that the lid 14 has a ribbing on the inner side, which, when the lid is closed, protrudes out towards the containment seat 5 passing through the access opening of such a seat 5. Advantageously such a ribbing makes it possible to stop the applicators 2, arranged horizontally inside the seat 5, when the seat 5 is full of such applicators, from moving by exploiting the concavity of the lid 14 as movement space.

In FIGS. 8 to 12 a further variant embodiment of the container 3 is shown, which, as well as having a different external shape compared to the containers already described, has some differences which shall be illustrated hereafter. In such a container 3, the coupling portion comprises, instead of a tray, a collar 11 which laterally protrudes from the main body 4 and having a first collar opening 13 adjacent to the access opening 9 of the containment seat 5 and a second collar opening 93 opposite the first collar opening 13. The laterally protruding collar 11, which advantageously has inclined outer walls, is such as to surround a portion 10_1 of the reservoir 10 suitable for being received and held, for example through shape coupling, in a receiving seat 12 which represents the inner part of the laterally protruding collar 11. For this purpose, the reservoir 10 is preferably shaped so as to be able to be inserted inside the laterally protruding collar 11 on the side of the second collar opening 93. More preferably, the reservoir 10 comprises for this purpose a portion 10_1 with relatively smaller sizes (for example, narrower) compared to the remaining portion 10_2 of the reservoir with relatively bigger sizes (for example, wider) which is intended for being inserted inside the seat 12 on the side of the second opening 93.

In the container 3 of FIGS. 8-11, the lid 14 comprises a relatively fixed part 14_1 suitable for permanently obstructing a portion of the access opening 9 to the containment seat 5 and a relatively mobile part 142, which can twist with respect to said fixed part 14_1 and for example rotatably hinged to it (along the hinge 90), to removably obstruct the access opening 13 and the remaining portion of the access opening 9. Preferably, the relatively fixed part 14_1 and the relatively mobile part 14_2 are two parts of one same lid made in a single piece 14 and form a distinct piece from the remaining part of the container 3. For this purpose the lid 14 is, for example, a substantially plate-shaped body, made from plastic and equipped with a weakened line (or weakened hinge line 90) which separates the relatively fixed portion 14_1 from the relatively mobile portion 14_2. The lid 14 thus made is applied to the remaining part of the container 3, for example by locking the relatively fixed portion 14_1 near to a rim of the opening 9. The fixing can in any case be carried out through different means, for example through adhesive or through a plastic sheet band suitable for holding the relatively fixed part 14_1 fixed to the container 4. In normal use, the relatively mobile part 14_2 is made to rotate around the weakened hinge line 90 to allow or block access into the receiving seat 5 and into the opening 20 of the reservoir 10.

Based upon what has been described above, it is now possible to understand how a container 3, according to the present invention is able to satisfy the aforementioned requirements described with reference to the prior art. A container of the type described above can indeed be made at relatively low cost and is simple and reliable to use.

Without affecting the principle of the invention, the embodiments and the details, can be widely varied with respect to what has been described and illustrated purely as an example and not for limiting purposes, without for this reason departing from the scope of the invention as defined in the attached claims.

The invention claimed is:

1. A container for disposable applicators, comprising:
   a main body comprising a containment seat defined by at least one side wall and a bottom wall, accessible through a first access opening opposite said bottom wall, the containment seat being suitable for containing a plurality of disposable applicators; and a reservoir suitable for containing a substance to be applied to said disposable applicators, wherein:

the reservoir and the main body form two distinct pieces, the container further comprises a coupling portion projecting out from said at least one side wall towards an outside of the main body and suitable for coupling the reservoir with the main body, the coupling portion comprising a coupling seat suitable for holding the reservoir in position next to the containment seat, the coupling portion having inclined outer side walls so as to allow additional containers to be stacked interpenetrating each other when said reservoir is not coupled with said container and before said container is filled, and the coupling portion comprises a laterally protruding collar having a first collar opening adjacent to said containment seat, and a second collar opening opposite said first collar opening, the laterally protruding collar surrounding a portion of the reservoir so that said reservoir passes through said second collar opening when the reservoir is fastened to the main body.

2. The container according to claim 1, wherein the coupling portion comprises a tray suitable for housing said reservoir inside of said tray, beside said containment seat.

3. The container according to claim 1, wherein the reservoir is shaped such that the reservoir is adapted to be locked and held into said laterally protruding collar, and is shaped such that the reservoir is adapted to be partially inserted into said collar on a side of said second collar opening.

4. The container according to claim 1, wherein said inclined outer side walls are tapered so as to come together in a direction that leads from said first access opening towards said bottom wall.

5. The container according to claim 1, wherein the main body is made by moulding or injection and the reservoir is made by blowing.

6. The container according to claim 1, wherein the reservoir is a bottle.

7. A system comprising:
the container according to claim 1;
a plurality of disposable applicators housed in said containment seat of said container; and
a cosmetic and/or detergent and/or sanitizing substance contained inside said reservoir of said container;
wherein said disposable applicators are cotton swabs and are arranged substantially parallel to each other in said containment seat.

8. A process of making the container according to claim 1, the process comprising:
making said main body of said container by moulding or injection, and arranging said main body stacked on other main bodies of a same type, thereby forming a stack;
making said reservoir by blowing;
feeding said reservoir and said stack to a packaging machine;
filling said reservoir with said substance;
taking said main body out from said stack,
coupling said reservoir with said main body; and
filling said main body with said disposable applicators,
thus forming a container for disposable applicators, comprising:
a main body comprising a containment seat defined by at least one side wall and a bottom wall, accessible through a first access opening opposite said bottom wall, the containment seat being suitable for containing a plurality of disposable applicators; and
a reservoir suitable for containing a substance to be applied to said disposable applicators, wherein:
the reservoir and the main body form two distinct pieces,
the container further comprises a coupling portion projecting out from said at least one side wall towards an outside of the main body and suitable for coupling the reservoir with the main body, the coupling portion comprising a coupling seat suitable for holding the reservoir in position next to the containment seat, the coupling portion having inclined outer side walls so as to allow additional containers to be stacked interpenetrating each other when said reservoir is not coupled with said container and before said container is filled, and
the coupling portion comprises a laterally protruding collar having a first collar opening adjacent to said containment seat, and a second collar opening opposite said first collar opening, the laterally protruding collar surrounding a portion of the reservoir so that said reservoir passes through said second collar opening when the reservoir is fastened to the main body.

9. A container for disposable applicators, comprising:
a main body comprising a containment seat defined by at least one side wall and a bottom wall, accessible through a first access opening opposite said bottom wall, the containment seat being suitable for containing a plurality of disposable applicators; and
a reservoir suitable for containing a substance to be applied to said disposable applicators, wherein:
the reservoir and the main body form two distinct pieces,
the container further comprises a coupling portion projecting out from said at least one side wall towards an outside of the main body and suitable for coupling the reservoir with the main body, the coupling portion comprising a coupling seat suitable for holding the reservoir in position next to the containment seat, the coupling portion having inclined outer side walls so as to allow additional containers to be stacked interpenetrating each other when said reservoir is not coupled with said container and before said container is filled,
the coupling portion has a second access opening having a rim in common with said first access opening, said first access opening and said second access opening being substantially beside each other forming two partitions of one same single container opening, said container also comprising a lid suitable for removably obstructing said single container opening, and
the lid comprises a relatively fixed part suitable for permanently obstructing a portion of said first access opening and a relatively mobile part adapted to rotate with respect to said fixed part to removably obstruct said second access opening and a remaining portion of said first access opening.

10. The container according to claim 9, wherein the lid is rotatably hinged to the main body.

11. A container for disposable applicators, comprising:
a main body comprising a containment seat defined by at least one side wall and a bottom wall, accessible through a first access opening opposite said bottom wall, the containment seat being suitable for containing a plurality of disposable applicators; and
a reservoir suitable for containing a substance to be applied to said disposable applicators, wherein:
the reservoir and the main body form two distinct pieces,
the container further comprises a coupling portion projecting out from said at least one side wall towards an outside of the main body and suitable for coupling the reservoir with the main body to fasten the reservoir to the main body, the coupling portion comprising a coupling seat suitable for holding the reservoir in position next to the containment seat, the coupling portion having inclined outer side walls so as to allow additional containers to be stacked interpenetrating each other when said reservoir is not coupled with said container and before said container is filled, the coupling portion has a second access opening having a rim in common with said first access opening, said first access opening and said second access opening being substantially beside each other forming two partitions of one same single container opening, said container also comprising a lid suitable for removably obstructing said single container opening, and the reservoir has a top outer wall defining a withdrawal opening, said top outer wall being arranged when said reservoir is fastened to said main body at a lower height than said rim.

12. The container according to claim 11, wherein the withdrawal opening is surrounded by a first raised collar and wherein the lid comprises an opposite second protruding collar suitable for interfering in abutment with the first raised collar when the lid is in a closed position.

13. A container for disposable applicators, comprising:
a main body comprising a containment seat defined by at least one side wall and a bottom wall, accessible through a first access opening opposite said bottom wall, the containment seat being suitable for containing a plurality of disposable applicators; and
a reservoir suitable for containing a substance to be applied to said disposable applicators, wherein:
the reservoir and the main body form two distinct pieces,
the container further comprises a coupling portion projecting out from said at least one side wall towards an outside of the main body and suitable for coupling the reservoir with the main body to fasten the reservoir to the main body, the coupling portion comprising a coupling seat suitable for holding the reservoir in position next to the containment seat, the coupling portion having inclined outer side walls so as to allow additional containers to be stacked interpenetrating each other when said reservoir is not coupled with said container and before said container is filled,
the coupling portion has a second access opening having a rim in common with said first access opening, said first access opening and said second access opening being substantially beside each other forming two partitions of one same single container opening, said container also comprising a lid suitable for removably obstructing said single container opening, and
said lid is a rounded lid comprising an inner ribbing jutting out from an inner side of said lid towards the containment seat to pass through the first access opening of said containment seat.

* * * * *